United States Patent [19]

Hauser

[11] 4,114,434
[45] Sep. 19, 1978

[54] DEVICE FOR MEASURING THE ADHESION FORCES IN A CLOSURE SEAL FOR A CONTAINER AND A METHOD OF OPERATING THIS DEVICE

[75] Inventor: Ivo Hauser, White Plains, N.Y.

[73] Assignee: Societe d'Assistance Technique pour Produits Nestle, S.A., La Tour-de-Peilz, Switzerland

[21] Appl. No.: 795,031

[22] Filed: May 9, 1977

[30] Foreign Application Priority Data

May 19, 1976 [CH] Switzerland .......................... 6239/70

[51] Int. Cl.² ............................................ G01N 19/04
[52] U.S. Cl. ................................................ 73/150 R
[58] Field of Search ............... 73/150 A, 150 R, 88 B, 73/101

[56] References Cited

U.S. PATENT DOCUMENTS 3,527,093   9/1970   Sellers ................................. 73/150 R Primary Examiner—Richard C. Queisser
Assistant Examiner—Joseph W. Roskos
Attorney, Agent, or Firm—Watson, Leavenworth, Kelton & Taggart

[57] ABSTRACT

A device for measuring the adhesion forces in a closure seal of a container, the seal being formed by a membrane adhering to the neck of a container and by a pad retained at the base of the cover of the container, adhering together, wherein it comprises a plunger with an adhesive and equipped with lateral guides and disposed in the recess of a shoe of which the sides form inclined planes adapted to the guides of the plunger and of which the base is provided with means for retaining the pad, the shoe being connected to a dynamometer.

7 Claims, 2 Drawing Figures

DEVICE FOR MEASURING THE ADHESION FORCES IN A CLOSURE SEAL FOR A CONTAINER AND A METHOD OF OPERATING THIS DEVICE

This invention relates to the hermetic closure of containers, especially in the food industry. More particularly, the invention relates to a device for measuring the principal forces involved in the removal of a cover for separating the pad remaining in the cover and the membrane fixed to the neck of the container with which the pad formed a seal. The invention also relates to a method of operating this device.

It is known that containers, especially food containers, are frequently closed by means of a cover and their contents protected by means of a thin membrane made, for example, of a metallic foil and hermetically bonded to the neck of the container. This membrane is removed or at least unstuck by the user when the container is used for the first time. Thereafter the container will only be closed by the cover, at the bottom of which is placed a relatively rigid pad, for example of cardboard, which absorbs the tolerances of the closure system and which is applied by the cover to the neck of the container when the cover is pushed on or screwed down.

Before it is applied to the container, the membrane is fixed to the pad by means of a waxy material applied, for example, spotwise over the entire contact surface between the membrane and the pad which are generally substantially equal to one another in diameter. The membrane and pad thus form a seal disposed at the base of the cover and retained by hooks. After the container has been filled, the rim of its neck is coated with adhesive or gum and the cover is applied.

The membrane is then bonded to the rim of the neck and the pad is attached to the membrane by wax seals.

Now, when the container is opened for the first time, the pad has to be able to detach itself easily from the membrane. If it were to adhere too strongly to the membrane, it would either become detached from the rim of the cover in spite of the hooks or would rupture the membrane or even detach it from the neck of the container.

Measurements carried out on a certain number of samples of seals taken at random would enable the probable percentage of defective seals to be determined by means of statistical methods.

The object of the device according to the present invention is to measure the force required for removing the cover and separating the membrane from the pad of a certain number of sample seals.

The device according to the invention is distinguished by the fact that it comprises a plunger with an adhesive end equipped with lateral guides and disposed in the recess of a shoe of which the sides form inclined planes adapted to the guides of the plunger and of which the base is provided with means for retaining the pad, the shoe being connected to a dynamometer.

One preferred embodiment of the device according to the invention is illustrated in the accompanying drawings, wherein.

Figure 1:
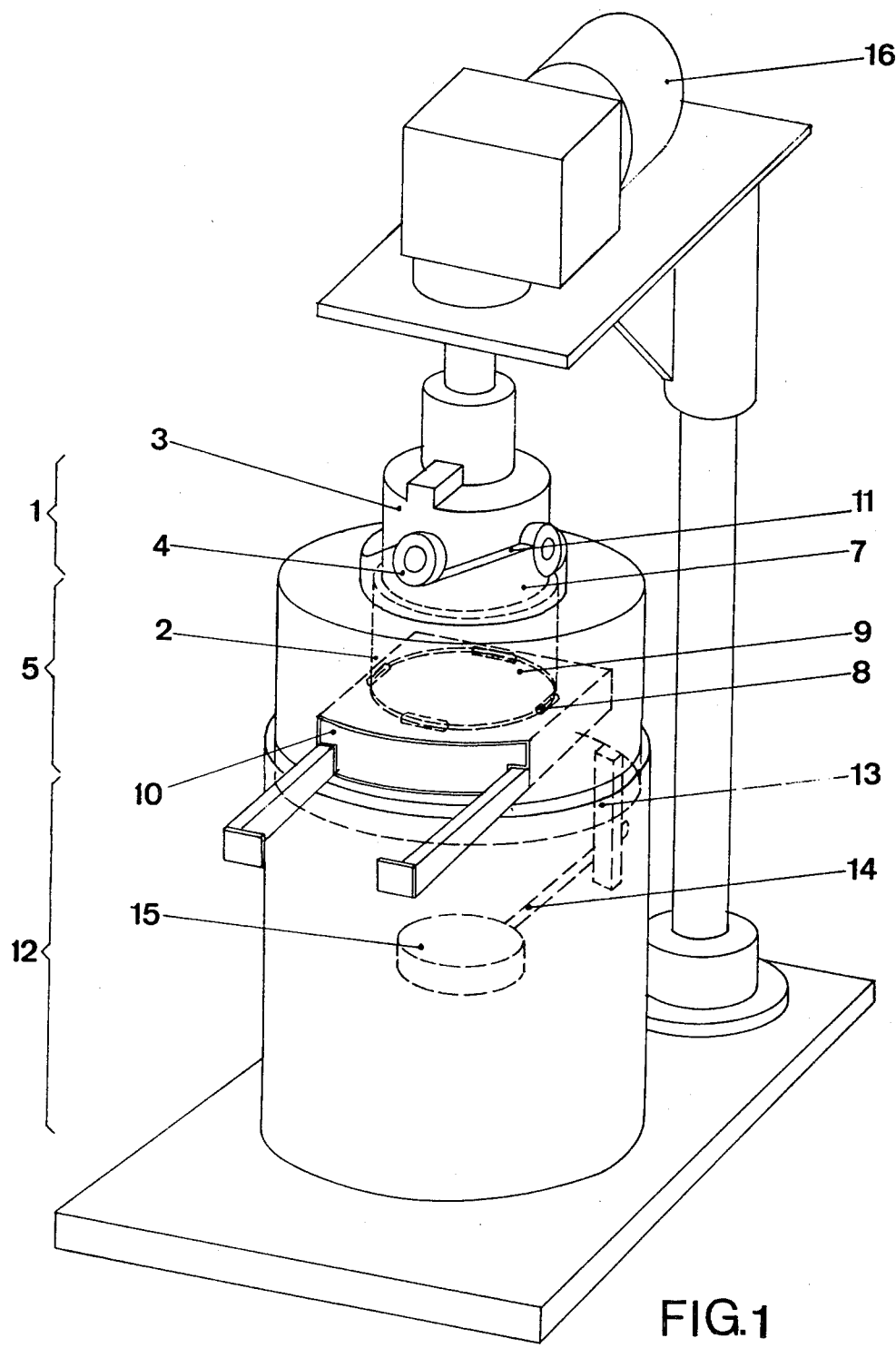
FIG. 1 is an axiometric view of the device as a whole.
Figure 2:
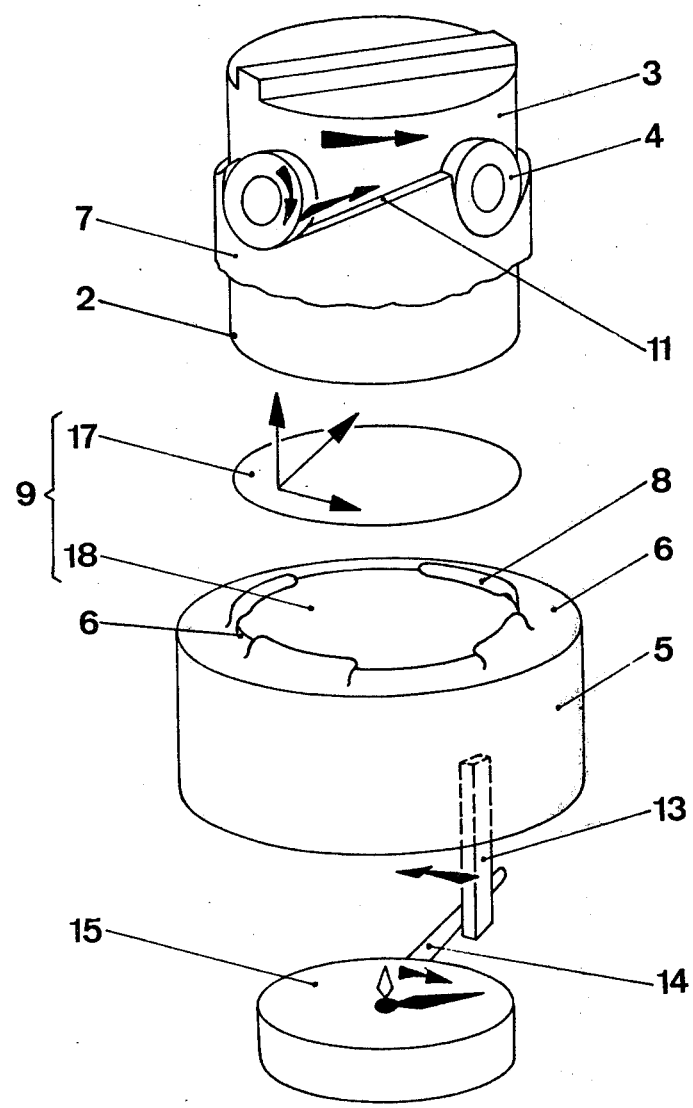
FIG. 2 is an exploded view in perspective showing the principal components of the device, arrows indicating the movement effected by the moving parts of the device.

As shown in the drawing, the device is formed by a plunger 1 having the dimensions of the neck of the container which it replaces (upside down). The plunger 1 is held in position by rollers 4 fixed to the body 3 of the plunger and, at its end 2, the plunger 1 comprises an adhesive surface.

The device further comprises a shoe 5 in which a recess has the dimensions of a cover adapted to the container, the base 6 of the recess corresponding to the base of the cover and the skirt 7 to the skirt of the cover. On its inner surface, the shoe 5 carries hooks 8 which retain the seal 9 at the base of the shoe 5 in the manner in which the seal is retained at the base of a cover. The skirt 7 is formed with an opening providing access to a slide 10 in which is disposed the seal 9 consisting of the membrane 17 and the pad 18. In addition, the free edge of the skirt 7 is formed with as many ramps 11 as the plunger 1 comprises rollers 4. The inclination of these ramps corresponds to the thread pitch of, for example, the cover of the container.

The shoe 5 is accommodated in a chassis 12 which enables it to rotate freely about its axis in order to enable an arm 13 fixed to the shoe to co-operate with a lever arm 14 actuating a dynamometer 15.

In the example illustrated, the plunger 1 is coupled for rotation to a motor 16 through a reduction gear.

The device according to the invention is operated as follows: the plunger is placed in the recess of a shoe at the base of which the seal has been previously positioned. The plunger then has a simultaneous rotational and lifting movement imparted to it, so that the pad retained at the base of the shoe is detached from the membrane adhesively secured to the plunger, the forces being measured by means of a dynamometer connected to the shoe.

The device according to the preferred embodiment is operated as follows:

With the slide 10 withdrawn, a seal 9 is applied to the slide with the membrane 17 on top. The slide is then introduced so that the seal 9 is disposed in the axis of the recess of the shoe 5. The plunger 1 is then introduced into the recess formed by the skirt 7. The plunger then rests with its rollers 4 on the ramps 11. Since it is coated with adhesive, the plunger 1 adheres to the membrane 17 diposed at the base 6 of the shoe. The motor 16 is then switched on.

The piston resting with its rollers 4 on the inclined surfaces 11 begins to make a simultaneous rotational movement and, under the effect of the rollers 4 and the ramps 11, a lifting movement relative to the shoe 5. In view of the fact that the seal 9 is generally somewhat smaller in thickness than the space separating the hooks 8 from the base 6 of the shoe, as is the case at the base of a cover, no significant friction is generated at the beginning of the operation. The seal 9 as a whole follows the movement of the plunger and moves away from the base 6 of the shoe in a helical movement. However, the forces begin to act when the seal 9 comes into contact with the hooks 8. From this moment, shearing forces begin to act on the waxy material between the membrane 17 entrained by the plunger 1 to which it adheres and the pad 18 prevented by the hooks 8 from following the movement. Under the effect of these forces, the arm 13 is pressed against the lever arm 14 which produces a deflection of the pointer of the dynamometer 15.

The plunger 1 guided by the rollers 4 continues its rotating and lifting movement until the point at which the waxy material ruptures is reached. It is then that the force applied to the lever arm 14 will have been at its maximum subsequently falling back to zero.

With the membrane 17 separated from the pad 18, the slide 10 is withdrawn and the pad 18 is replaced by a new seal 9 for the following test. The plunger 1 is withdrawn from the skirt 7 to remove the membrane 17 adhering thereto. The plunger, too, is then ready for the next test.

I claim:

1. A device for measuring the adhesion forces in a closure seal of a container, the seal being formed by a membrane adhering to the neck of a container and by a pad retained at the base of the cover of the container, adhering together, said device comprising a plunger with an adhesive end equipped with lateral guides, a skirt encircling said plunger and having an upper edge in the form of inclined planes adapted to receive the lateral guides of the plunger, and a shoe having a base which is provided with means for retaining the pad, rotation of said plunger about a fixed axis causing said plunger to move axially and thereby effect separation of said membrane from said pad, the shoe being connected to a dynamometer whereby the force required to effect such separation is transmitted to said dynamometer.

2. A device as claimed in claim 1, wherein the lateral guides of the plunger (1) are rollers (4).

3. A device as claimed in claim 1, wherein the plunger (1) is connected to a reduction motor (16).

4. A device as claimed in claim 1, wherein the shoe (5) rests freely in a chassis (12) and a lever arm (14) is connected to the dynamometer and the shoe is provided with an arm (13) designed to co-operate with said lever arm 5. A device as claimed in claim 1, wherein the outer lateral wall of the shoe (5) is provided with a slide (10) at the level of the base (6) where same retains said pad 6. A device as claimed in claim 5, wherein the slide (10) is mounted for sliding movement radially of said axis to withdraw said shoe for insertion of an adhered together membrane and pad therein.

7. A device as claimed in claim 1, wherein the shoe (5) is provided with hooks (8) near the base (6) for retaining said pad.

* * * * *

UNITED STATES PATENT OFFICE
CERTIFICATE OF CORRECTION

PATENT NO. : 4,114,434
DATED : September 19, 1978
INVENTOR(S) : Ivo Hauser

It is certified that error appears in the above-identified patent and that said Letters Patent are hereby corrected as shown below:

Foreign application priority data, change number to read --6239/76--.

Signed and Sealed this

Twenty-sixth Day of December 1978

[SEAL]

Attest:

RUTH C. MASON
Attesting Officer

DONALD W. BANNER
Commissioner of Patents and Trademarks